US00PP35885P2

(12) United States Plant Patent
Ault

(10) Patent No.: US PP35,885 P2
(45) Date of Patent: Jun. 25, 2024

(54) ***BAPTISIA* PLANT NAMED 'LAST DANCE'**

(50) Latin Name: ***Baptisia* hybrid**
Varietal Denomination: Last Dance

(71) Applicant: James Robert Ault, Libertyville, IL (US)

(72) Inventor: James Robert Ault, Libertyville, IL (US)

(73) Assignee: CHICAGOLAND GROWS, INC., Glencoe, IL (US)

( * ) Notice: Subject to any disclaimer, the term of this patent is extended or adjusted under 35 U.S.C. 154(b) by 0 days.

(21) Appl. No.: 18/377,345

(22) Filed: Oct. 6, 2023

(51) Int. Cl.
*A01H 5/02* (2018.01)
*A01H 6/00* (2018.01)

(52) U.S. Cl.
USPC ..... Plt./263.1
CPC ..... *A01H 6/00* (2018.05)

(58) Field of Classification Search
USPC ..... Plt./263.1
CPC ..... A01H 5/02
See application file for complete search history.

*Primary Examiner* — Kent L Bell
(74) *Attorney, Agent, or Firm* — Penny J. Aguirre

(57) ABSTRACT

A new cultivar of *Baptisia* plant of hybrid origin that is named 'Last Dance' and is characterized by its narrowly upright plant habit with foliage lacking on the lower half of the stems, its dense foliage (especially towards the tips of the shoots), its flowers that emerge white in color and turn to creamy yellow in color, and its late flowering period (commences and ends late).

3 Drawing Sheets

Botanical classification: *Baptisia* hybrid.
Cultivar Designation: 'Last Dance'.

BACKGROUND OF THE INVENTION

The present invention relates to a new and distinct cultivar of *Baptisia* plant of hybrid origin and will be referred to hereinafter by its cultivar name, 'Last Dance'. The new cultivar represents a new false indigo, an herbaceous perennial plant grown for ornamental landscape use.

The new cultivar was discovered as a chance seedling by the Inventor in June of 2003 in a trial field in Glencoe, IL. The trial field had been planted with seeds of unnamed and unpatented plants of hybrid origin and of *Baptisia leucantha*. The parents of the new cultivar are unknown.

Asexual propagation of the new cultivar was first accomplished by the Inventor by division in spring of 2006 in Glencoe, Illinois. Asexual propagation by division and stem cuttings has determined that the characteristics of the new cultivar are stable and reproduced true to type in successive generations.

SUMMARY OF THE INVENTION

The following traits have been repeatedly observed and are determined to be the characteristics of the new cultivar. These attributes in combination distinguish 'Last Dance' as a unique cultivar of *Baptisia*.

1. 'Last Dance' exhibits a narrowly upright plant habit with foliage lacking on the lower half of the stems.
2. 'Last Dance' exhibits dense foliage, especially towards the tips of the shoots.
3. 'Last Dance' exhibits flowers that emerge white in color and turn to creamy yellow in color.
4. 'Last Dance' exhibits a late flowering period (commences and ends late).

'Last Dance' can be most closely compared to the *Baptisia* cultivars 'Ivory Towers' (U.S. Plant Pat. No. 26,827) and 'Vanilla Cream' (U.S. Plant Pat. No. 25,663). 'Ivory Towers' and 'Vanilla Cream' are both similar to 'Last Dance' in having white flowers and very upright plant habits. 'Vanilla Cream' is also similar to 'Last Dance' in plant size. 'Ivory Towers' differs from 'Last Dance' in having an earlier blooming period, leaves that are slightly larger in size, and stems that are purple in color. 'Vanilla Cream' differs from 'Last Dance' in having an earlier blooming period, leaves that are much larger in size, and a much smaller overall plant size.

BRIEF DESCRIPTION OF THE DRAWINGS

The accompanying color photographs illustrate the overall appearance and distinct characteristics of 8-year-old plants of the new *Baptisia* as grown outdoors in a trial garden in Glencoe, Illinois.

The photograph in FIG. 1 provides a side view of the plant habit of two plants of 'Last Dance' in bloom.

Figure 1:
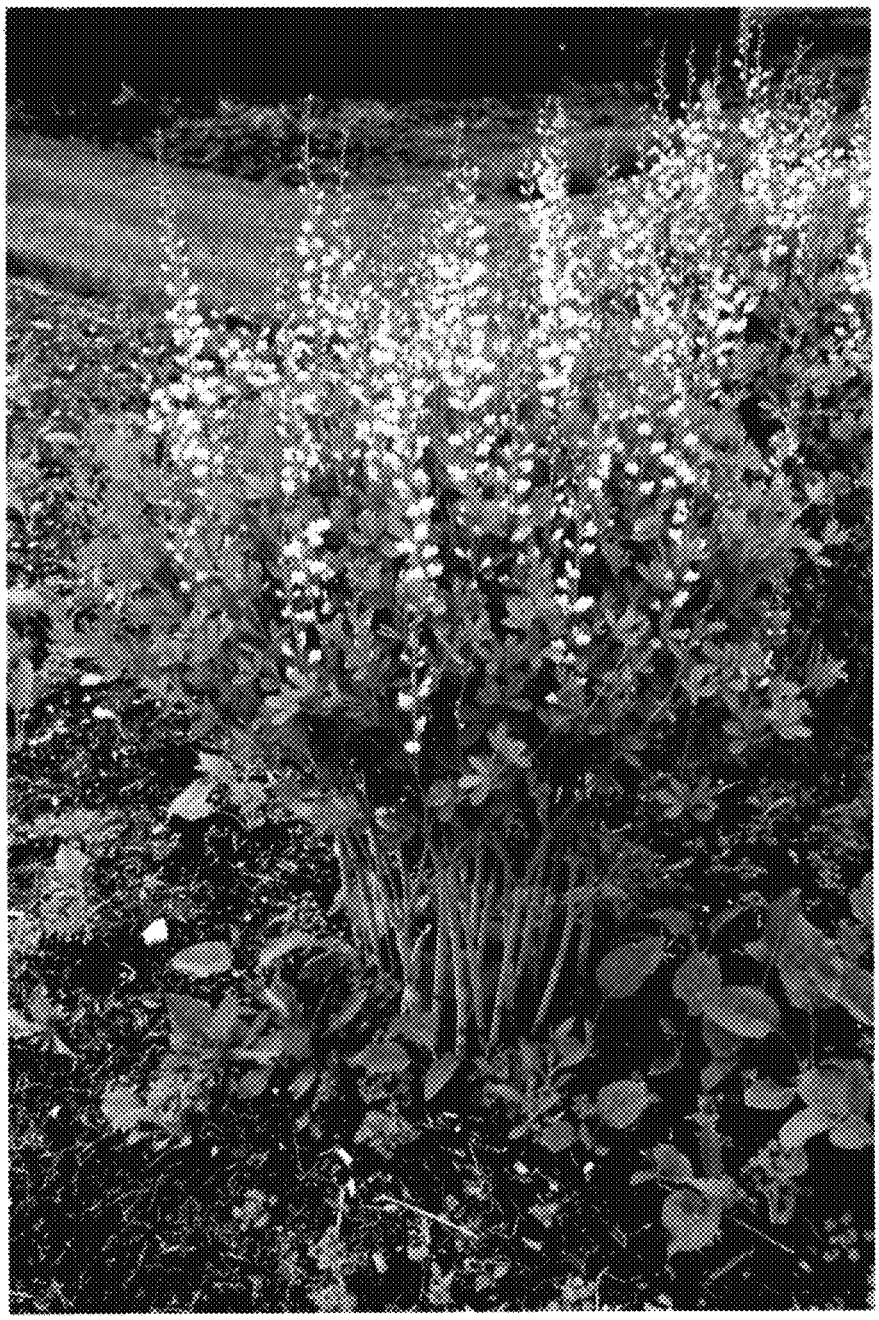
Figure 2:
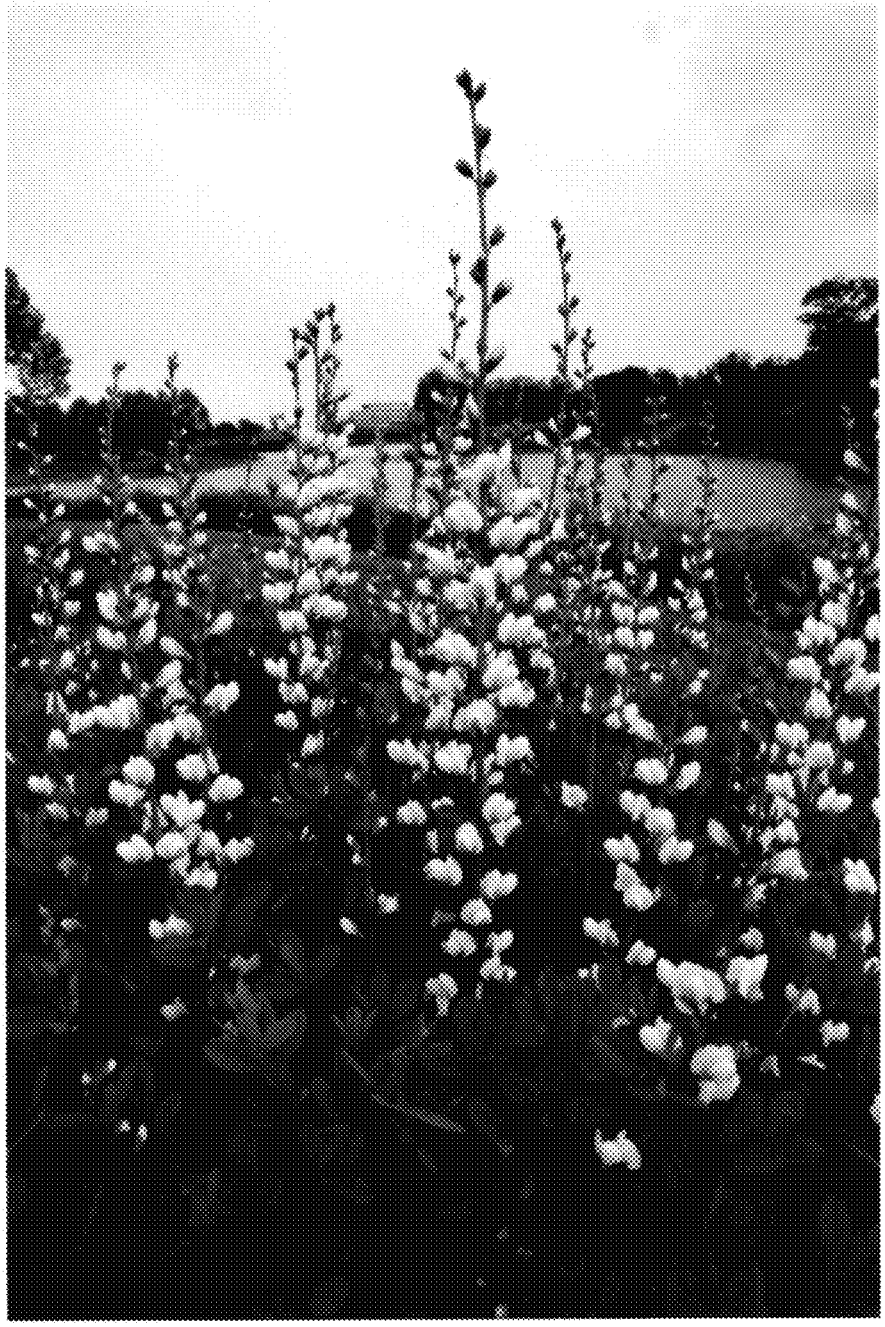

The photograph in FIG. 2 provides a close-up view of the inflorescences of 'Last Dance'.

Figure 3:
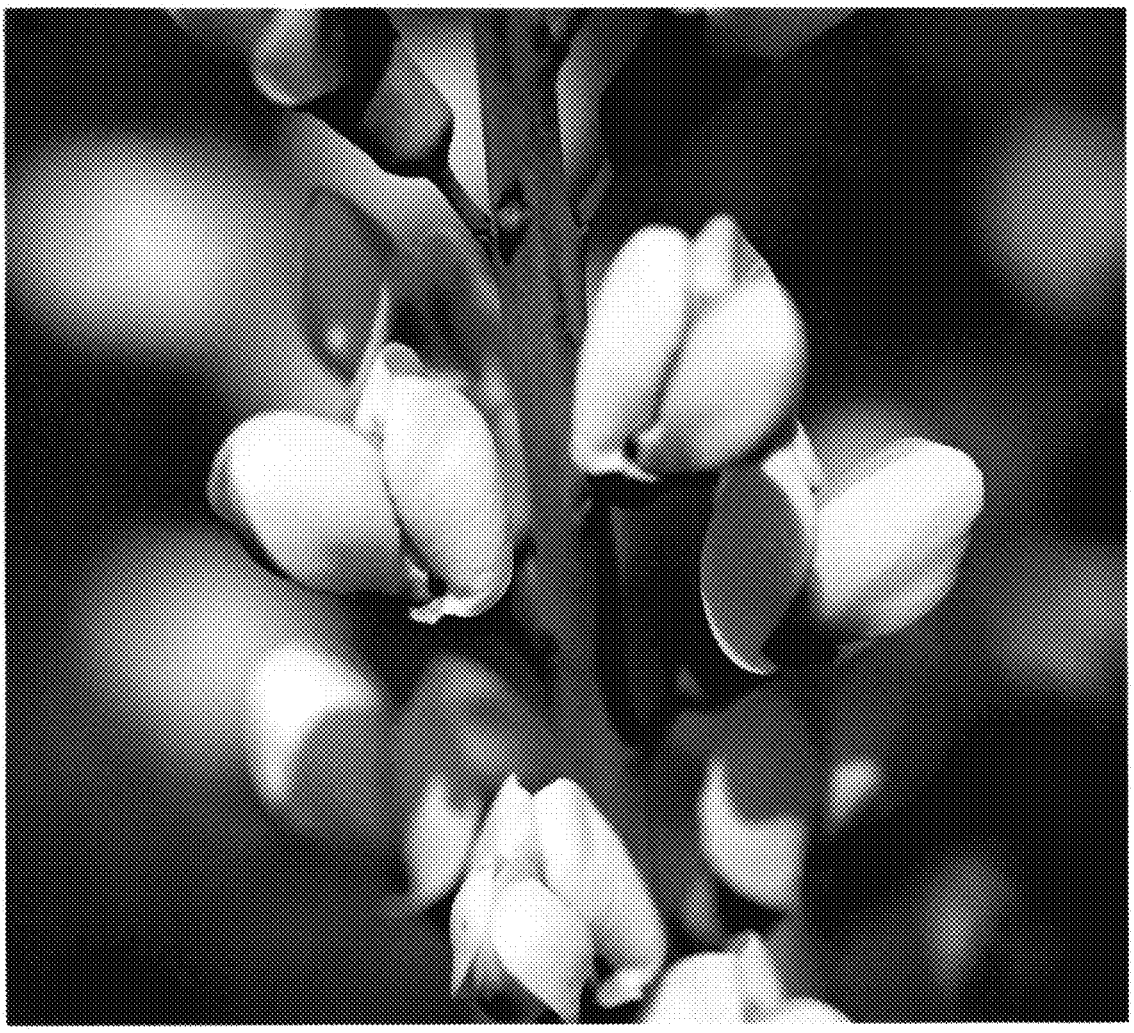

The photograph in FIG. 3 provides a close-up view of the flowers of 'Last Dance'.

The colors in the photographs may differ slightly from the color values cited in the detailed botanical description, which accurately describe the colors of the new *Baptisia*.

DETAILED BOTANICAL DESCRIPTION

The following is a detailed description of the new cultivar as observed on 1-year-old plants of the new *Baptisia* as grown in 4-inch containers in cold frames in Glencoe, Illinois. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—4 weeks, early June to late June in Glencoe, Illinois, late blooming; 7 to 10 days later that what is typical for *Baptisia* cultivars.

*Plant type.*—Herbaceous perennial.

*Plant habit.*—Narrowly upright, dense foliage, and stems that are leafless on the lower half of the stems.

*Height and spread.*—Reaches an average of 26 cm in height and 18 cm in spread as a one-year-old plant in a container and 1.07 m in height and spread as a mature plant in the landscape.

*Hardiness.*—At least in U.S.D.A. Zones 4 to 8.

*Diseases and pests.*—No resistance or susceptibility to diseases or pests has been observed.

*Root description.*—Deep rooted, fibrous, 161C in color.

*Propagation.*—Stem cuttings and division.

*Time required for root initiation.*—An average of 6 weeks for root initiation and 9 weeks to produce a young plant from a rooted cutting.

*Growth rate.*—Moderate.

Branch description:

*Branching habit.*—Moderately branched.

*Branch size.*—Main stem; average of 14 cm in length, 3 mm in width, secondary; average of 14 cm in length and 2 mm, tertiary; an average of 5 cm in length and 1 mm in width.

*Branch number.*—An average of 3 main stems and 4 secondary stems per main branch on a one-year-old plant.

*Branch shape.*—Oval.

*Branch color.*—Young; 145A, mature; 146A.

*Branch surface.*—Glabrous, satiny, slightly glossy, and slightly glaucous.

*Branch strength.*—Main; strong, lateral; strong to moderately strong, tertiary; weak.

*Branch aspect.*—Main; vertical to slightly outward, lateral; held in a 40° angle from main branch, tertiary; held in a 20° angle from lateral branch.

Foliage description:

*Leaf shape.*—Fan-shaped in overall outline.

*Leaf division.*—3-palmate.

*Leaf size.*—Average of 5 cm in length and 9 cm in width.

*Leaflet size.*—An average of 5 cm in length and 2 cm in width (widest point).

*Leaf quantity.*—About 10 per stem.

*Leaflet shape.*—Oblanceolate.

*Leaflet base.*—Cuneate.

*Leaflet apex.*—Broadly acute.

*Leaflet venation.*—Pinnate pattern, color on upper surface matches leaf surface and is slightly translucent, color on lower surface matches leaf surface except the main vein is 151A.

*Leaflet margins.*—Entire.

*Leaf attachment.*—Petiolate.

*Leaf arrangement.*—Alternate.

*Leaflet surface.*—Both surfaces glabrous, matte, and satiny.

*Leaflet color.*—Upper surface 147B, lower surface 138B.

*Leaf internode.*—Average of 3 cm.

*Petioles.*—Average of 5 mm in length and 1 mm in width, clasping to stem and slightly cupped, 145A in color, surface is glabrous and glossy.

*Stipules.*—Narrowly lanceolate in shape, reflexed to stem, base is truncate to stem, apex is apiculate, average of 1 cm in length and 2 mm in width on mature leaves, both surfaces, color; 138A, base 145C.

Flower description:

*Inflorescence type.*—Terminal racemes of pea-shaped flowers on main branch.

*Inflorescence size.*—Average of 38 cm in length and 6 cm in width.

*Lastingness of inflorescences.*—3 to 4 weeks.

*Flower size.*—About 2 cm in depth and about 1.5 cm in diameter.

*Flower fragrance.*—None.

*Flower number per inflorescence.*—Average of 35.

*Peduncle.*—Oval in shape, up to 53 cm in length and an average of 5 mm in width, 144A and light vertical strips of N144A in color, top 194A, surface is glabrous, satiny and moderately glaucous, flower internode length averages 2 cm in length.

*Pedicel.*—Average of 5 mm in length, about 1 mm in width, round in shape, 143C in color, glabrous and glossy surface.

*Flower buds.*—Kidney-shaped, average of 2 cm in length, 6 mm in width, color; 145A, top lightly flushed with 147A, before burst; 8D, lightly flushed with 8C.

*Flower type.*—Papilionaceous.

*Calyx.*—Campanulate, about 6 mm in depth and 5 mm in diameter, both surfaces 145A in color, inner surface glabrous and glossy, outer surface glabrous, matte, and slightly glaucous.

*Sepals.*—4, fused, apex is triangular in shape, 3 mm in width and 5 mm in depth with an acute and sometimes notched apex, both surfaces 144A in color, inner surface glabrous and glossy, outer surface glabrous, matte, and slightly glaucous, margins entire and densely covered with soft pubescent hairs, 193A in color.

*Corolla features.*—Papilionaceous (4 segments) with a keel, a banner and 2 lateral wings, lateral wings; obelliptic in shape, slightly cupped, flared to expose keel, 1.5 cm in length and 6 mm in width, rounded apex, base is cuneate and fused, margins are entire and slightly undulate, both surfaces matte, satiny, very slightly rugose, color: when opening and fully open upper and lower surface; NN155A, base 149D, keel; 2 segments surrounding reproductive organs, oblong (slightly oblique) in shape with rounded apex and narrow base that is slightly fused, 2 cm in length and 7 mm in width, margins are entire, both surfaces matte, satiny, very slightly rugose, color: when opening and fully open upper and lower surface; 150D, outer edges flushed with 150C and 145A, banner; orbicular and kidney shaped, base and center fused, reflexed, 1.5 cm in length and 2 cm in width, apex is rounded, both surfaces matte and satiny, margins are entire and slightly undulate, rolled under, color: when opening and fully open inner surface; NN155A, center and base 142B and covered with a fountain shape of tiny dots that are 203A and 200A, when opening and fully open outer surface; NN155A, center and base 142B.

*Receptacle*.—Disk-shaped, gelatinous, 144A in color, about 3 mm in diameter and 2 mm in depth.

Reproductive organs:

*Gynoecium*.—Pistil; 1, style; 6 mm in length, 154A in color, surface is moderately glossy and glabrous, thick and round in shape, stigma; inconspicuous, ovary; superior, flattened and linear in shape, 143A in color, 5 mm in length and 2 mm in width.

*Androecium*.—Stamens; 10, filament; 1.6 cm in length, 1 mm in width, glabrous and glossy surface, 145B and 145C in color, anther; dorsifixed, kidney shaped, 1 mm in length, 0.5 mm in width, 25B in color, pollen; abundant in quantity and 21A in color.

*Fruit and seed*.—Capsules quickly drop when forming and do not develop and were not available for data collection.

It is claimed:

1. A new and distinct cultivar of *Baptisia* plant named 'Last Dance' as herein illustrated and described.

* * * * *